United States Patent
Chang et al.

(10) Patent No.: US 10,624,602 B2
(45) Date of Patent: Apr. 21, 2020

(54) MEDICAL IMAGING DEVICE AND METHOD CONTROLLING ONE OR MORE PARAMETERS OF A MEDICAL IMAGING DEVICE

(71) Applicant: Siemens Healthcare GmbH, Erlangen (DE)

(72) Inventors: Yao-jen Chang, Princeton, NJ (US); Terrence Chen, Princeton, NJ (US); Birgi Tamersoy, Erlangen (DE); Vivek Kumar Singh, Princeton, NJ (US); Susanne Oepping, Erlangen (DE); Ralf Nanke, Neunkirchen Am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 72 days.

(21) Appl. No.: 15/949,148

(22) Filed: Apr. 10, 2018

(65) Prior Publication Data
US 2018/0296177 A1    Oct. 18, 2018

(30) Foreign Application Priority Data
Apr. 13, 2017 (EP) .................................. 17166493

(51) Int. Cl.
*A61B 6/00* (2006.01)
*A61B 6/06* (2006.01)
(Continued)

(52) U.S. Cl.
CPC ................ *A61B 6/545* (2013.01); *A61B 6/06* (2013.01); *A61B 6/08* (2013.01); *A61B 6/40* (2013.01);
(Continued)

(58) Field of Classification Search
CPC .... A61B 6/06; A61B 6/08; A61B 6/40; A61B 6/5211; A61B 6/5294; A61B 6/542; A61B 6/545; G06T 2207/10028
See application file for complete search history.

(56) References Cited

U.S. PATENT DOCUMENTS

| 9,895,131 B2 | 2/2018 | Chang |
| 2003/0120145 A1* | 6/2003 | Schmitz ............... A61B 6/4233 600/407 |

(Continued)

FOREIGN PATENT DOCUMENTS

| EP | 2954843 A1 | 12/2015 |
| WO | WO 2005009243 A1 | 2/2005 |
| WO | WO 2014033614 A1 | 3/2014 |

OTHER PUBLICATIONS

Redmon, Joseph et al.: "You Only Look Once: Unified, Real-Time Object Detection", in: CVPR, 2016, pp. 779-788.
(Continued)

*Primary Examiner* — David J Makiya
*Assistant Examiner* — Soorena Kefayati
(74) *Attorney, Agent, or Firm* — Harness, Dickey & Pierce, P.L.C.

(57) ABSTRACT

Embodiments include a medical imaging device and a method controlling one or more parameters of a medical imaging device. In one embodiment, a method includes receiving image data representing a first image of an object to be imaged using the radiation source and detecting a plurality of positions of respective predetermined features in the first image. Based upon the detected positions, a boundary of an imaging area of the object to be imaged is determined. Based on the determined boundary, one or more parameters of the radiation source unit are controlled.

27 Claims, 8 Drawing Sheets

(51) Int. Cl.
*A61B 6/08* (2006.01)
*G06T 7/73* (2017.01)
*G06T 7/00* (2017.01)

(52) U.S. Cl.
CPC .......... *A61B 6/5211* (2013.01); *A61B 6/5294* (2013.01); *G06T 7/0012* (2013.01); *G06T 7/73* (2017.01); *A61B 6/542* (2013.01); *G06T 2207/10028* (2013.01); *G06T 2207/10116* (2013.01); *G06T 2207/30004* (2013.01)

(56) References Cited

U.S. PATENT DOCUMENTS

| | | | | |
|---|---|---|---|---|
| 2014/0355735 A1* | 12/2014 | Choi | ............... | A61B 6/544 378/8 |
| 2015/0104092 A1 | 4/2015 | Flohr | | |
| 2015/0228071 A1* | 8/2015 | Jockel | ............... | A61B 6/08 382/132 |
| 2015/0245804 A1* | 9/2015 | Kieft | ............... | A61B 6/06 378/147 |
| 2015/0313558 A1* | 11/2015 | Melman | ............... | G21K 1/04 378/62 |
| 2015/0327821 A1* | 11/2015 | Hu | ............... | A61B 6/5205 378/62 |
| 2015/0327830 A1* | 11/2015 | Hu | ............... | A61B 6/06 378/8 |
| 2015/0327832 A1* | 11/2015 | Hu | ............... | A61B 6/547 378/62 |
| 2016/0113617 A1* | 4/2016 | Herrmann | ............... | A61B 6/42 378/207 |
| 2016/0232653 A1* | 8/2016 | Hishida | ............... | G01N 23/04 |
| 2016/0374639 A1* | 12/2016 | Becker | ............... | A61B 6/4464 378/95 |
| 2017/0032527 A1* | 2/2017 | Murthy | ............... | H04N 5/33 |
| 2017/0055925 A1* | 3/2017 | Lee | ............... | A61B 6/465 |
| 2017/0112460 A1* | 4/2017 | Merckx | ............... | A61B 6/547 |
| 2017/0119338 A1* | 5/2017 | Merckx | ............... | A61B 6/08 |
| 2017/0273639 A1* | 9/2017 | Iscoe | ............... | G06F 3/04815 |
| 2017/0303879 A1* | 10/2017 | Maack | ............... | A61B 6/4233 |
| 2018/0116622 A1* | 5/2018 | Jan | ............... | G01N 23/04 |
| 2019/0000564 A1* | 1/2019 | Navab | ............... | A61B 6/03 |

OTHER PUBLICATIONS

Zhuown, Tu et al; "Probabilistic boosting-tree: Learning discriminative models for classification, recognition, and clustering"; Computer Vision, 2005; ICCV 2005 Tenth IEEE International Conference on; vol. 2; IEEE; pp. 1-9; 2005.

Extended European Search Report dated Feb. 13, 2018.

* cited by examiner

MEDICAL IMAGING DEVICE AND METHOD CONTROLLING ONE OR MORE PARAMETERS OF A MEDICAL IMAGING DEVICE

PRIORITY STATEMENT

The present application hereby claims priority under 35 U.S.C. § 119 to European patent application number EP17166493.1 filed Apr. 13, 2017, the entire contents of which are hereby incorporated herein by reference.

FIELD

At least one embodiment of the invention generally relates in one aspect to a method controlling one or more parameters of a medical imaging device comprising a radiation source. In another embodiment, the invention generally relates to a medical imaging device. In further embodiments, the invention generally relates to a computer program product and/or a computer-readable medium.

BACKGROUND

Medical images devices, such as X-ray imaging devices, may provide flexibility and convenience for medical imaging because the radiation source can be moved freely to focus on a region of interest on an object to be imaged, such as a body part of a patient.

Conventionally, adjustment of a collimator for collimating the radiation beam and positioning of the radiation source, is performed manually. In known imaging devices, a technician moves, for example, an X-ray tube and aligns a radiation field projected from the collimator to the object center and then adjusts the light field size to match the size of a region of the body part to be imaged. Typically, several iterations of manual adjustment may be needed, which may be time consuming.

SUMMARY

The inventors have discovered that there is a need to automate the process to improve throughput and the efficiency of such imaging devices.

At least one embodiment of the invention is directed to a method; a medical imaging device; and a computer program product. The claims are related to further aspects and embodiments of the invention.

At least one embodiment of the invention relates to a method of controlling one or more parameters of a medical imaging device comprising a radiation source unit, the method comprising:
  receiving image data representing a first image of an object to be imaged using the radiation source unit to form a second image;
  detecting a plurality of positions of respective predetermined features in the first image;
  determining a boundary of an imaging area of the object to be imaged on the basis of the detected positions; and
  controlling one or more parameters of the radiation source unit on the basis of the determined boundary.

At least one embodiment of the invention relates in one aspect to a medical imaging device comprising:
  a processor arranged to:
    receive image data representing a first image of an object to be imaged using a radiation source unit of the medical imaging device;
    determine a boundary of an imaging area of the object to be imaged on the basis of detected positions of respective predetermined features in the first image; and
    control one or more parameters of the radiation source unit on the basis of the determined boundary.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

Figure 1:
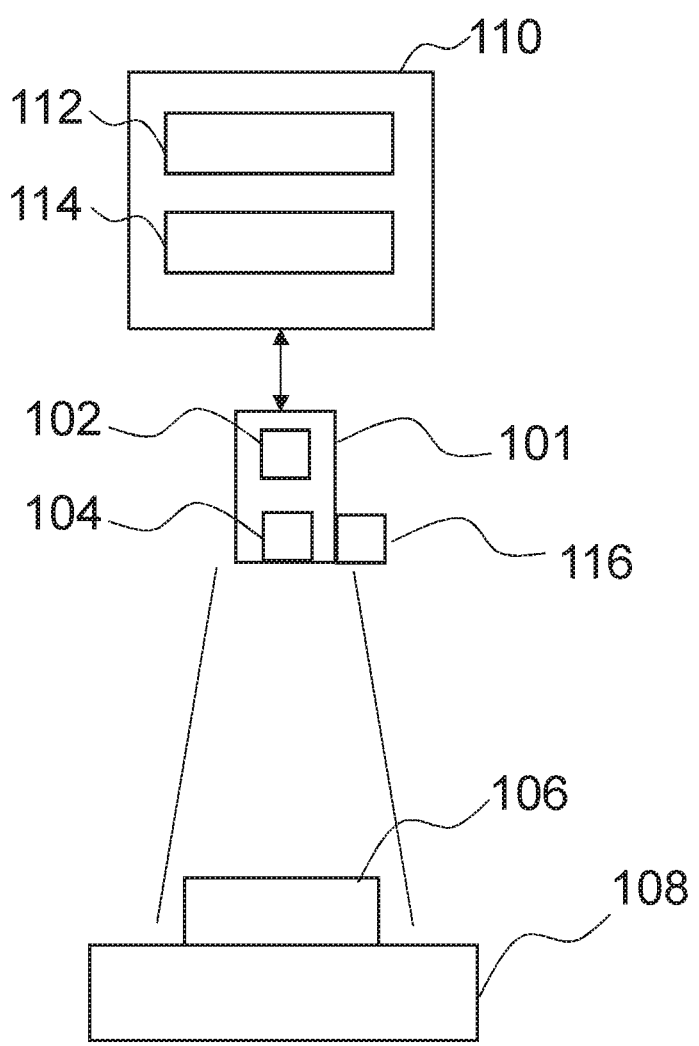
FIG. 1 shows a medical imaging device according to one embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method of controlling one or more parameters of a medical imaging device comprising a radiation source unit, the method comprising:
  receiving image data representing a first image of an object to be imaged using the radiation source unit to form a second image;
  detecting a plurality of positions of respective predetermined features in the first image;
  determining a boundary of an imaging area of the object to be imaged on the basis of the detected positions; and
  controlling one or more parameters of the radiation source unit on the basis of the determined boundary.

One embodiment of the invention relates in one aspect to a method, the method further comprising:
  determining an object size and/or an object orientation of the object to be imaged on the basis of the detected positions.

One embodiment of the invention relates in one aspect to a method, the method further comprising:
  determining the object orientation on the basis of an angle of a line intersecting two or more of the detected positions; and
  orientating the boundary of the imaging area of the object to correspond with the object orientation.

One embodiment of the invention relates in one aspect to a method, wherein the one or more parameters of the radiation source unit comprise a position of the radiation source unit and/or one or more collimator settings of a collimator of the radiation source unit.

One embodiment of the invention relates in one aspect to a method, wherein detecting the positions comprises:
  evaluating one or more portions of the first image with respect to a model of predetermined features;
  assigning a probability value to each of the one or more portions of the first image on the basis of the evaluation; and
  determining that one or more of the one or more portions of the first image corresponds with a the predetermined feature on the basis of the corresponding assigned probability value.

One embodiment of the invention relates in one aspect to a method, the method further comprising:
  identifying a background portion of the first image and a foreground portion of the first image based on data in the received image data representing one or more image channels; and
  determining the boundary on the basis of the identifying.

One embodiment of the invention relates in one aspect to a method, the method further comprising:
  determining whether a first part of the foreground portion of the first image meets the boundary; and
  if the first part of the foreground portion of the first image meets the boundary, adjusting the boundary to encompass the first part.

One embodiment of the invention relates in one aspect to a method, the method further comprising:
  determining whether there is a background portion of the first image between the first part of the first image and the boundary; and
  if there is a background portion of the first image between the first part of the first image and the boundary, adjusting the boundary so as to reduce the size of the background portion.

One embodiment of the invention relates in one aspect to a method, wherein the object to be imaged is a body part of a human or animal subject and the predetermined features comprise anatomical features of the subject and the first part comprises a distal end of the object to be imaged.

At least one embodiment of the invention relates in one aspect to a medical imaging device comprising:
  a processor arranged to:
    receive image data representing a first image of an object to be imaged using a radiation source unit of the medical imaging device;
    determine a boundary of an imaging area of the object to be imaged on the basis of detected positions of respective predetermined features in the first image; and
    control one or more parameters of the radiation source unit on the basis of the determined boundary.

One embodiment of the invention relates in one aspect to a medical imaging device, wherein the one or more parameters comprise a position and/or orientation of the radiation source unit.

One embodiment of the invention relates in one aspect to a medical imaging device, wherein the radiation source unit comprises a collimator for collimating a beam of radiation emitted from the radiation source unit, wherein the processor is arranged to control one or more collimator settings on the basis of the determined boundary.

One embodiment of the invention relates in one aspect to a medical imaging device, comprising a camera arranged to generate the first image, the camera being different from the radiation source unit.

One embodiment of the invention relates in one aspect to a medical imaging device, wherein the medical imaging device is an X-ray radiography device and the radiation source unit comprises an X-ray source.

At least one embodiment of the invention relates in one aspect to a computer program product comprising a computer program, the computer program being loadable into a memory unit of a data processing system, including program code sections to make the data processing system execute at least one embodiment of the method according to an aspect of the invention when the computer program is executed in the data processing system.

The computer program product of at least one embodiment can be, for example, a computer program or comprise another element apart from the computer program. This other element can be hardware, for example a memory device, on which the computer program is stored, a hardware key for using the computer program and the like, and/or software, for example a documentation or a software key for using the computer program.

The medical imaging device can be, for example, be selected from the group consisting of a computed tomography device, a magnetic resonance imaging device, a molecular imaging device, a SPECT-device, a PET-device and combinations thereof. The medical imaging device can be, for example, a combination of an imaging modality and a therapy modality, in particular a radiation therapy modality.

Reference is made to the fact that the described methods and the described medical imaging device are merely preferred example embodiments of the invention and that the invention can be varied by a person skilled in the art, without departing from the scope of the invention provided it is specified by the claims.

FIG. 1 is a diagram illustrating an imaging device 100 according to an embodiment of the present invention. The imaging device comprises a radiation source unit 101 comprising a radiation source 102 arranged to emit a beam of radiation through a collimator 104. The collimator 104 is arranged to collimate the beam of radiation. For example, the collimator 104 may be arranged to restrict a spatial extent of the radiation beam in one or more directions perpendicular to a direction of propagation of the beam.

The radiation source 102 may, for example, be a source of high energy electromagnetic radiation. For example the radiation source 102 may be an X-ray generator arranged to emit X-ray radiation.

The radiation source 102 is arranged to be moveable such that the beam of radiation may be directed at an object 106 to be imaged. The collimator 104 may be adjustable such that the extent of the beam may cover more or less of the object 106.

The object 106 may, in use, be located on an imaging platform 108. The imaging platform 108 may, for example, comprise, or be arranged to receive, a detector arranged to detect radiation emitted from the radiation source 102. In other examples, the imaging platform 108 may be arranged to receive a cassette containing radiographic or photographic film reactive to the radiation emitted from the radiation source 102.

The imaging device 100 may comprise a controller 110 for controlling one or more parameters of the radiation source unit 101. For example, the controller 110 may control a position and/or an orientation of the radiation source unit 101 to control a position from which radiation is emitted from the radiation 102 and/or one or more settings of the collimator 104. For example, the controller 110 may be arranged to generate control signals for controlling drive motors or other electromechanical actuators connected to the radiation source unit 101 and/or the collimator 104 to control the position orientation, and/or extent of an emitted beam of radiation.

The controller 110 may be implemented using hardware and/or software. In some examples, the controller 110 may comprise a processor 112 programmed to perform the functions of the controller 110.

The controller 110 may include a memory 114 arranged to store data in the form of a model that is trained by implementing a machine learning algorithm prior to installation and use of the imaging device 100 in an operation setting. For example, the model may be trained by supplying sample images to the model and, with input from a human operator, the machine learning algorithm may learn to detect features in the sample data. In some examples, the available sample data may be augmented by rotating and/or flipping the sample images.

Furthermore, the memory 114 may store a computer program executable by the processor 112, to perform the methods described herein, and specifically the methods described below with reference to FIGS. 2 and 4.

The memory 114, may be any suitable form of memory. For example, the memory 114 may comprise volatile memory, such as random access memory (RAM) and/or non-volatile memory such as read only memory (ROM) or flash memory. Furthermore, the memory 114 might comprise multiple, separate, memory devices and may comprise a combination of volatile and non-volatile memory. In some examples, certain component of the invention, such as the computer program and/or the model, may be stored in one memory device, while other components may be stored in another memory device.

The machine learning algorithm may be any suitable algorithm. For example, the machine learning algorithm may be a probabilistic boosting tree (PBT) algorithm, which enables a model to be trained to detect an object in an image and to detect positions of predetermined features (i.e. landmarks) in the image.

In another implementation, the machine learning algorithm may be a convolutional neural network (CNN) algorithm, which enables a model to be trained to detect an object in an image, to classify the detected object (i.e. identify an object type) and to detect positions of predetermined features (i.e. landmarks) in the image. So, for example, the controller 110 may classify whether the foreground object is from left hand, right hand, left foot, or right foot.

In some examples, information regarding the type of object (e.g. that the object is a human hand or foot) may be provided to the model by a human operator when applying the model. In other examples, information regarding the type of object may not be input by a human operator and may instead be learned or inferred by the model.

In some embodiments, as depicted in FIG. 1, the imaging device 100 comprises a camera 116, such as, for example, an optical camera. For example the camera 116 may be a 2D camera arranged to provide one or more color channels or a 2D camera arranged to provide a grayscale image. In other examples, the camera 116 may be a 3D camera arranged to provide one or more color channels and one or more depth channels. In some embodiments, the imaging device 100 may comprise one or more interfaces (not shown) for receiving a connection to a camera not permanently connected to the imaging device 100.

The camera 116 may be mechanically connected to the radiation source unit 101, as shown in FIG. 1, so that the camera 116 moves with the radiation source unit 101.

Accordingly, images generated by the camera 116 will include an area that will be irradiated by radiation source 102 wherever the radiation source unit 101 is located.

Figure 2:
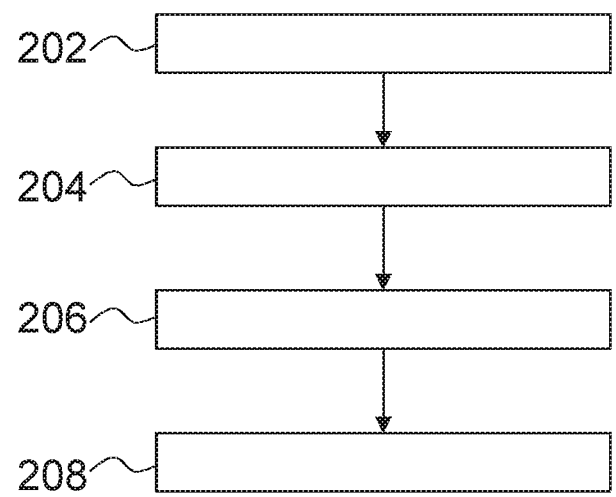
FIG. 2 shows a workflow diagram illustrating a method according to one embodiment of the invention.

FIG. 2 is a flow diagram depicting a method 200 of controlling one or more parameters of the medical imaging device 100. The method 200 may, for example, be implemented by software or firmware executed by the controller 110 described above with reference to FIG. 1.

At block 202, the controller 110 receives image data representing a first image of the object 106 to be imaged using the radiation source to form a second image. For example, the image data may be received from the camera 116.

At block 204, the controller 110 determines a plurality of positions of predetermined features in the first image. For example, the controller 110 may evaluate one or more portions of the first image with respect to a model of positions of predetermined features. In some examples, the controller 110 may evaluate regions of the first image comprising one or more pixels. The regions of the first image may be defined by a moving window, for example. Based on the evaluation with respect to the model, the controller 110 may assign, to each of the one or more portions of the first image, a probability value relating to a probability that a given portion of the image corresponds to a position of a predetermined feature. Once each portion of the first image is assigned a probability value, the controller 110 may determine that one or more of the one or more portions of the first image corresponds with a position of a predetermined feature based on the corresponding assigned probability values. For example, portions of the first image with a probability value exceeding a threshold probability value may be identified as a position of a predetermined feature.

Alternatively, portions of the first image with a highest probability value of relating to a particular type of predetermined feature may be identified as position of the predetermined features. For example, a portion of the image with the highest probability value of being knuckle may be identified as one position of a predefined feature and a portion of the image with the highest probability value of being wrist may be identified as another position of a predefined feature.

The predetermined features may be, for example, landmarks of the object 106 to be imaged, as defined when the model is trained, as described above, by supplying sample images to the model with input from a human operator. In some examples, the predetermined features may be anatomical features (i.e. body parts) of a human or animal subject. For example, the positions of predetermined features may correspond to a wrist, an ankle, a finger, a toe, a joint, or any other body part.

In order to assist the controller 110 in determining the positions of predetermined features, in some examples an operator of the imaging device 100 may provide additional input via an interface device such as a keyboard, mouse, or touch-screen device (not shown) to indicate to the controller 110 the classification of the object 106 that is to be imaged. For example, the operator may provide input indicating that the object 106 to be imaged is a human hand or a human foot. In some examples, the controller 110 may use this additional input in the determining the predetermined features by, for example, considering in the evaluation with respect to the model, only sample data relevant to an object type corresponding with the object type defined by the additional input of the operator. By the operator providing such information, the computation burden placed on the controller may be reduced.

In particular, in some example, the controller 110 may request via a user interface (not shown) input, from the operator of the imaging device 100, specifying the type of object 106 to be imaged. However, in other examples, the controller 110 may determine the type of object without input from the operator of the imaging device 100, which may reduce the burden on the operator of the imaging device 100.

At block 206, the controller 110 determines a boundary of an imaging area of the object 106 to be imaged on the basis of the detected positions of predetermined features.

In some examples, the controller 110 may determine a size and/or an orientation of an object 106 to be imaged based on the detected positions of predetermined features. For example, the controller 110 may determine, based on the positions of known landmarks or features in the image (and perhaps information regarding the type of the object in the image), that the object 106 is likely to be a certain size and is at a certain orientation.

For example, the controller 110 may determine an angle of a line intersecting two (or more) positions of predetermined features and determine the orientation of the object 106 in the image based on the angle of that line. In some examples, the controller 110 may orientate the first image to align the first image according to an axis of the object 106 to be imaged. For example, in the case where the object 106 to be imaged is a human hand, the first image may be rotated such that a longitudinal axis of the hand, as defined by a line joining the knuckle joint of the middle finger with the center of the wrist, is parallel with an edge of a subsequently applied boundary. In another example, in the case where the object 106 to be imaged is a human foot, the first image may be rotated such that a longitudinal axis of the foot, as defined by a line joining the joint the joint of the middle toe and the ankle, is parallel with an edge of a subsequently applied boundary.

Alternatively, the controller 110 may orientate the boundary of the imaging area to align the boundary with an axis of the object 106 to be imaged. For example, in the case where the object 106 to be imaged is a human hand, an edge of the boundary may be arranged to be parallel with a longitudinal axis of the hand, as defined by a line joining predetermined features at the knuckle joint of the middle finger with the center of the wrist.

At block 208, the controller 110 controls one or more parameters of the radiation source unit 101 on the basis of the determined boundary. For example, the controller 110 may determine a mapping between parameters defining the boundary and one or more parameters of the radiation source unit 101. For example, the controller 110 may determine a position and/or orientation of the radiation source unit 101 based on a mapping of the position of the boundary and/or the controller 110 may determine one or more collimator settings of the collimator 105 based on a mapping of one or more edges of the boundary.

The one or more parameters of the radiation source unit 101 may include a position and/or orientation of the radiation source unit 101 and/or one or more settings of the collimator 104. These parameters may be set such that the area of the object 106 exposed to radiation from the radiation source 102 is the area enclosed by the boundary box. In other examples, the one or more parameters of the radiation source unit 101 may include a relative position of the radiation source with respect to the object 106 to be imaged. For example, in some applications, such as fluoroscopy, the radiation source unit 101 may be fixed and the object 106 to be imaged may located on a table that is moveable relative to the radiation source 102.

Figure 3A:
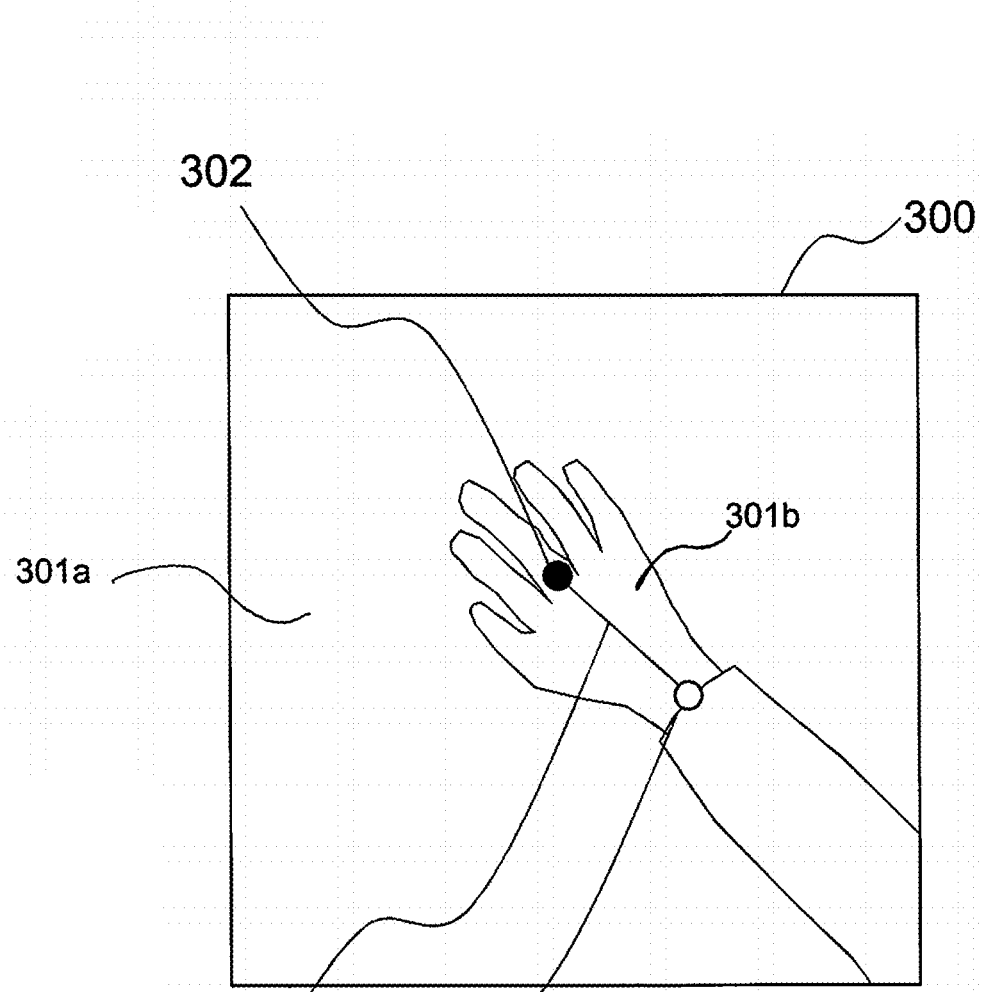
FIG. 3a shows a representation of an image, which may be a photograph or digital image, of an example object to be imaged by an imaging device according to one embodiment of the invention.

FIG. 3*a* is an image 300 depicting an example of the object 106 to be imaged using an imaging device 100. In the example shown in FIG. 3*a*, the object 106 is a human hand; however, in other examples, the object 106 may be another anatomical feature of a human or animal, or any other object.

In the example shown in FIG. 3*a*, the controller 110 may determine a first position of a predetermined feature 302 corresponding to a knuckle joint of the hand and a second position of a predetermined feature corresponding to a wrist joint of the hand.

Also shown in FIG. 3*a* is a line 306 joining the first position of a predetermined feature 302 and the second position of a predetermined feature 304.

Figure 3B:
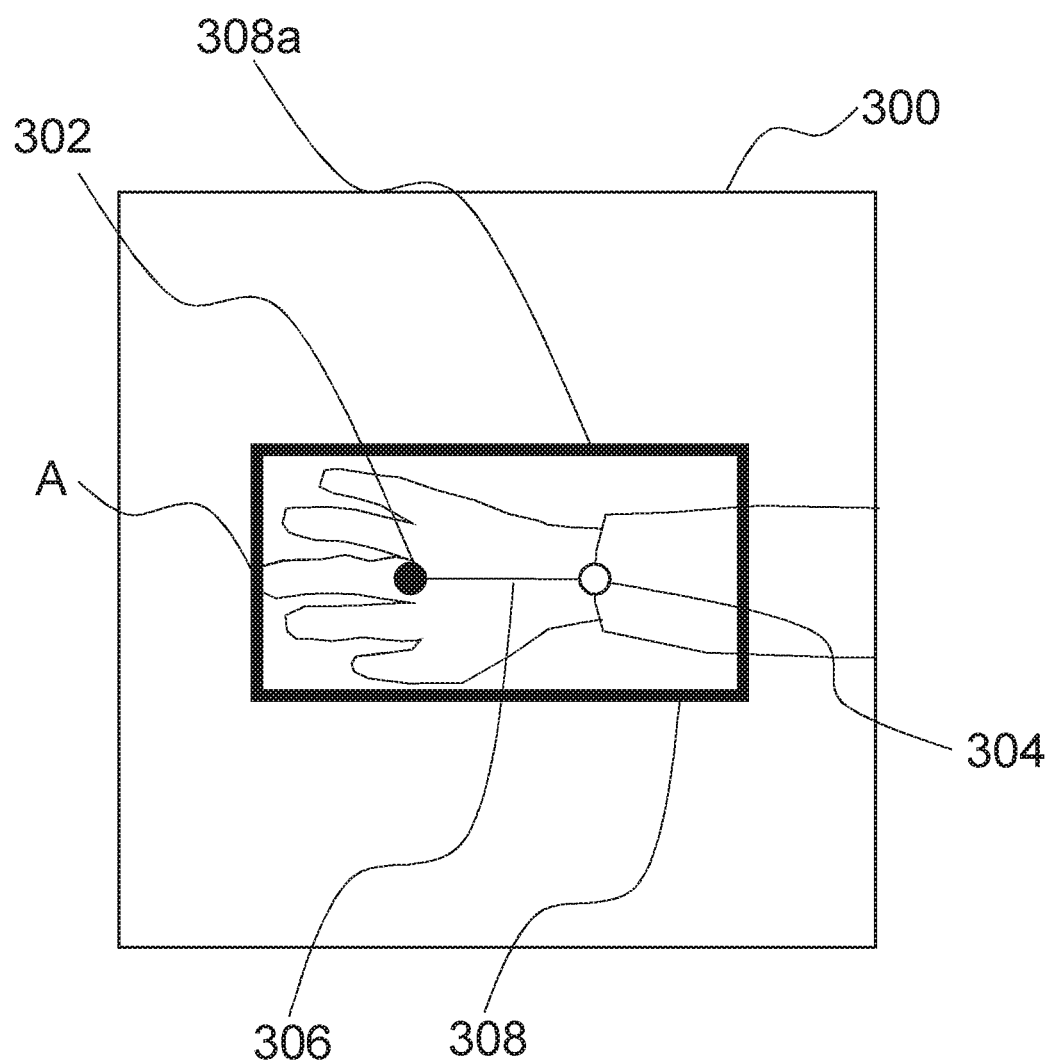
FIG. 3b shows a representation of an image, which may be a photograph or digital image, of an example object to be imaged by an imaging device according to one embodiment of the invention.

As shown in FIG. 3*b*, based on an angle of that line, the controller 110 may orientate the image 300 such that an edge 308*a* of the image 300 is aligned with the object 106 to be imaged by the imaging device 100. The boundary 308 is then determined as described above with reference to FIG. 2. For example, in the case where the object 106 to be imaged is a human hand, an edge of the boundary 308 may be arranged to be parallel with a longitudinal axis of the hand, as defined by a line joining the knuckle joint of the middle finger with the center of the wrist. In another example, in the case where the object 106 to be imaged is a human foot, an edge of the boundary 308 may be arranged to be parallel with a longitudinal axis of the foot, as defined by a line joining the joint between the middle toe and the center of the ankle.

Aligning the boundary 308 with the object 106 to be imaged in this way may, in some examples, reduce the proportion of the area that is exposed to radiation that does not contain the object 106 so as to minimize the amount of radiation required to generate a useful image.

Figure 3C:
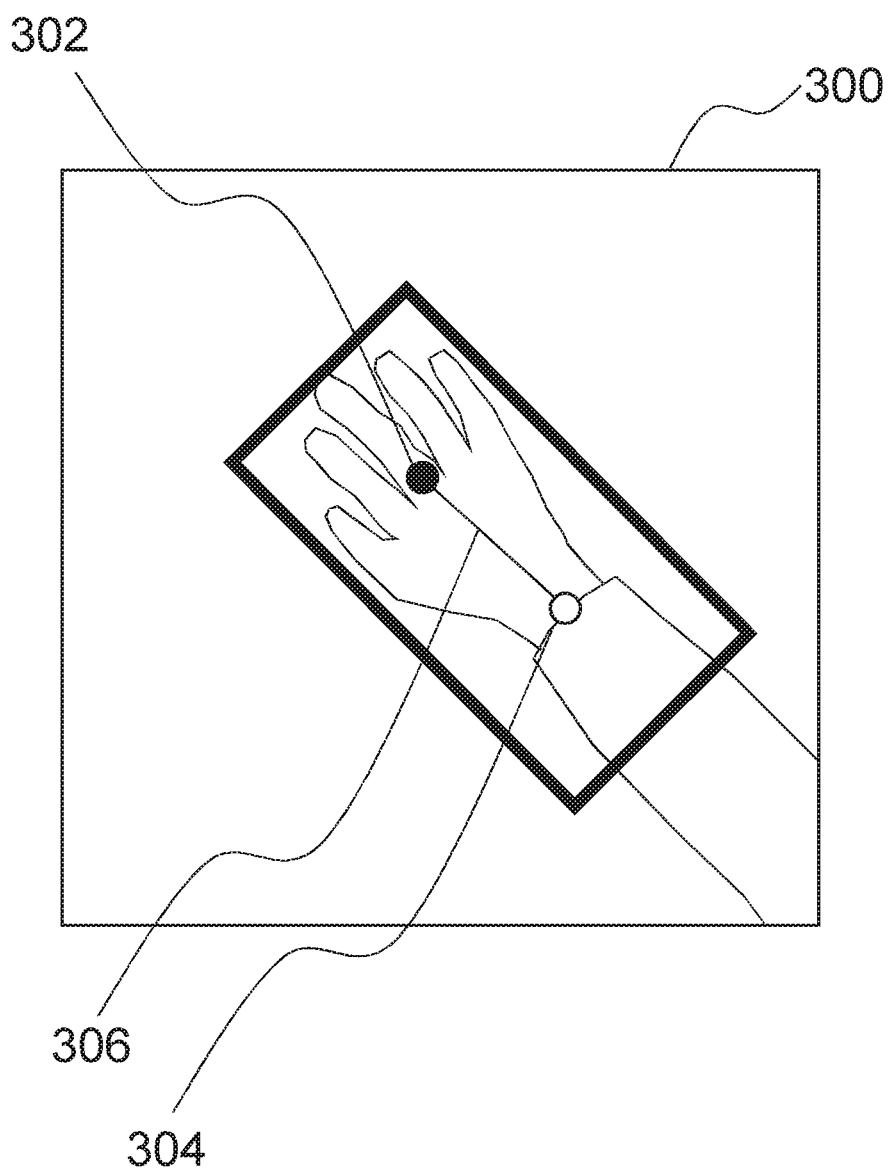
FIG. 3c shows a representation of an image, which may be a photograph or digital image, of an example object to be imaged by an imaging device according to one embodiment of the invention.

As shown in FIG. 3*c*, once the boundary determined for the image aligned such that the image 300 is aligned with the object 106 to be imaged by the imaging device 100, the image 300 may be rotated again to its original orientation such that the boundary is aligned and oriented with the radiation source unit 101. As the camera 116 is connected to (and moves with) the radiation source unit 112, the controller 110 may then determine a mapping between coordinates defining the boundary in the image 300 and the one or more parameters of the radiation source unit 101, because the image is aligned with the radiation source unit 101.

In applications such as medical imaging, proper diagnosis often relies on complete imaging of a body part. Omission of any area, no matter how small the area, may result in an unusable image that must be re-taken. For example, if an image of an injured hand omits the fingertips, the image may need to be repeated to include the fingertips. In applications that use ionizing radiation, such as X-ray imaging, repeating the imaging process exposes the subject to additional, potentially harmful, radiation. However, adding a large margin around an object 106 to be imaged may also be undesirable, as again it may result in additional exposure to radiation since the amount of radiation required to generate a useful image may be higher. Furthermore, adding a large margin around an object 106 to be imaged may also expose other parts of the object 106 to radiation unnecessarily. For example, if the object 106 is a body part of a human subject, adding a larger than necessary margin may expose other body parts to radiation. In some cases, these other body parts may be more sensitive (e.g. prone to cellular mutation) than the body part of the object 106 to be imaged.

In order to optimize the boundary 308 to image an area that includes all of the object 106 to be imaged but minimizes excess exposure to radiation, the boundary 308 determined by the method 200 described above with reference to FIG. 2 may be further refined on the basis of information provided in the first image.

In some examples, the controller 110 may distinguish between a background portion 301*a* of the first image 300 and a foreground portion 301*b* of the first image based on the one or more image channels, as shown in FIG. 3*a* for example. This may enable, for example, the controller 110 to set an initial constraint on the area of the image that is of interest (i.e. the area of the image that is likely to contain the object 106 to be imaged by the imaging device 100).

In the case of an image produced by a 2D camera (i.e. having only color channels) the controller 110 may distinguish between foreground and background on the basis of a difference in color. Typically, the object 106 to be imaged (such as the human hand of FIG. 3*a* for example) is located on the imaging platform 108 when the first image 300 is taken. The imaging platform 108 typically has a uniform appearance and color (which may be known) which enables the controller 110 to identify portions of the image which are background portions 301*a* and to distinguish the object 106 (such as the human hand of FIG. 3*a*). in the foreground portion 301*b* from the background portion 301*a*.

Similarly, in the case of an image produced by a 3D camera, the controller may distinguish between background and foreground on the basis of a difference in color (or intensity) and may additionally or alternatively distinguish between background and foreground on the basis of a difference in depth. In particular, the imaging platform 108 is typically flat and at a known depth and the controller 110 may determine that locations at that known depth are background and location forward of that depth are foreground.

In some examples, the controller 110 may determine an initial boundary 308 and refine the initial boundary 308 to ensure that the boundary 308 encompasses all features in the foreground portion 301*b* of the first image but does not encompass excessive amounts of the background portion 301*a* of the first image 300.

Figure 4:
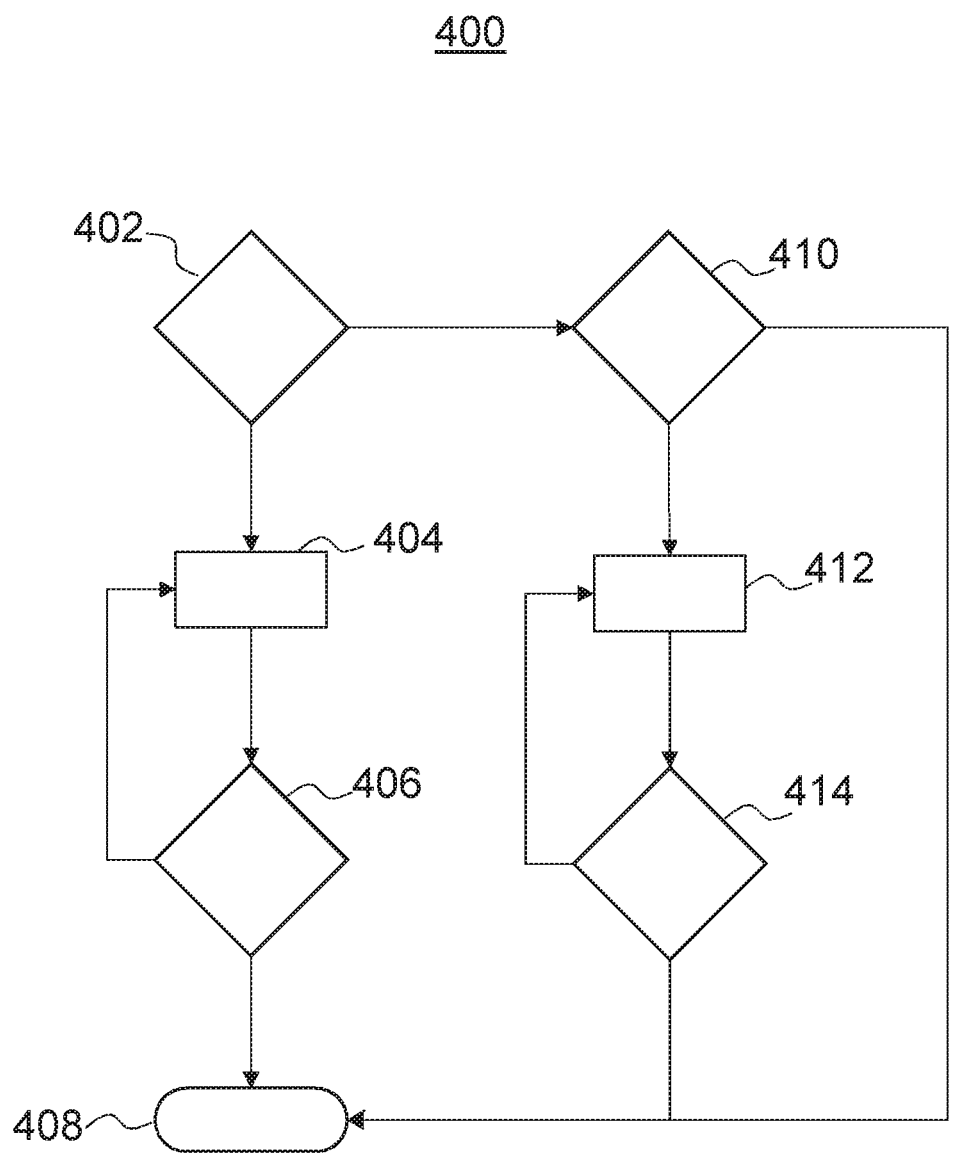
FIG. 4 shows a workflow diagram illustrating a method according to one embodiment of the invention.

FIG. 4 shows a method 400 by which the initial boundary 308 may be refined.

In most medical imaging applications, the object 106 to be imaged is connected to the rest of the subject's body (for example, a hand is connected to an arm by a wrist). Accordingly, in such cases, there will always be some part of the foreground portion of the image that meets the boundary 308. In the example shown in FIG. 3*b*, that foreground portion of the image intersects the boundary 308 at an opposite edge to the point A; however, depending on the positioning of the object 106 to be imaged that foreground portion of the image may intersect the boundary 308 on another edge of the boundary 308.

In such examples, the controller 110 may identify a first part of the object 106 to be imaged, and determine the boundary so as to encompass that part. For example, the controller may identify that one of the predetermined features is at a distal feature of the object 106 to be imaged (e.g. a knuckle joint of a hand) with respect to a proximal feature (e.g. a wrist joint connecting the hand to an arm), and identify a distal end of the object to be imaged (i.e. the outermost portion of the object to be imaged), such as the fingertips of a hand, on the basis of the first position. The controller 110 may then determine the boundary to ensure that the distal end of the object is encompassed by the boundary. For example, one or more of three side boundaries of the boundary near the finger region (determined from the detected positions of predetermined features) may be moved to extend the area defined by the boundary.

At block 402, the controller 110 determines whether a portion of the foreground portion of the first image, distal to an identified position of a predetermined feature that relates to a distal feature (referred to as a "first part" below), meets the boundary 308, for example as shown at point A in FIG. 3b.

If, at block 402, the controller 110 determines that the first part meets the boundary 308, the controller 110 proceeds to block 404.

At block 404, the controller 110 adjusts one or more edges of the boundary 308 to enlarge an area of the first image encompassed by the boundary 308 before proceeding to block 406. For example, the controller 110 may move each of the three edges closest to a distal feature of the object 106 to be imaged away from the corresponding position of the predefined feature by a predefined amount.

At block 406, the controller 110 determines again whether the first part meets the boundary 308.

If at block 406 it is determined that the first part meets the boundary 308, the controller 110 returns to block 404 and adjusts one or more edges of the boundary 308 to enlarge an area of the first image encompassed by the boundary 308, subsequently returning again to block 406.

If, at block 406, the controller 110 determines that no portion of the first part meets the boundary 308, the controller 110 proceeds to block 408 to end the refinement method 400.

Figure 5:
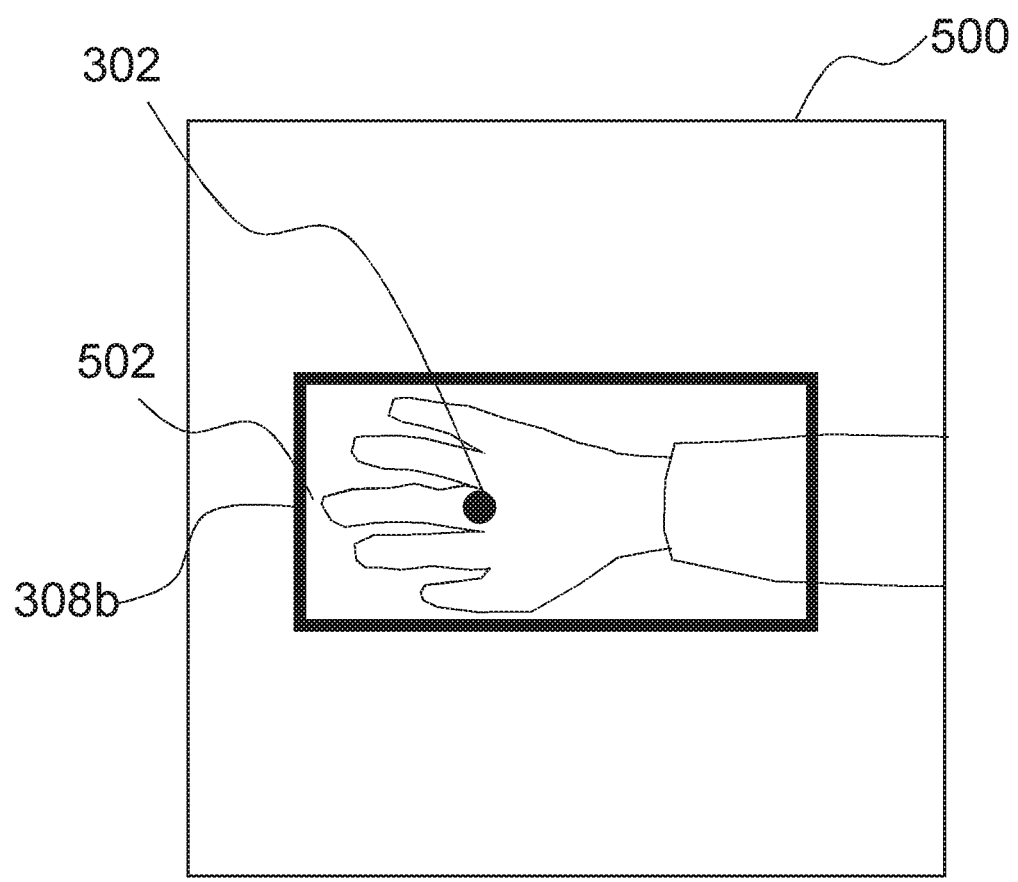
FIG. 5 shows a representation of an image, which may be a photograph or digital image, of an example object to be imaged by an imaging device according to one embodiment of the invention.

FIG. 5 shows an example of an image 500 for which the controller 110, having refined the boundary 308 shown in FIG. 3b, has adjusted an edge 308b of the boundary 308 for which the controller 110 has determined that a portion of the first part meets the boundary 308. As a result of the controller 110 adjusting the edge 308b of the boundary 308, there is a region 502 of background between the foreground and the boundary 308. This ensures that no part of the distal part of the object 106 is not imaged when the one or more parameters of the radiation source unit 101 and/or the collimator are controlled on the basis of the defined boundary 308.

If, however, at block 402 the controller 110 determines that no portion of the first part meets the boundary 308, the controller may proceed to block 410.

At block 410, the controller 110 determines whether there is a background portion of the first image between the first part and the boundary 308 that exceeds a threshold amount.

Figure 6:
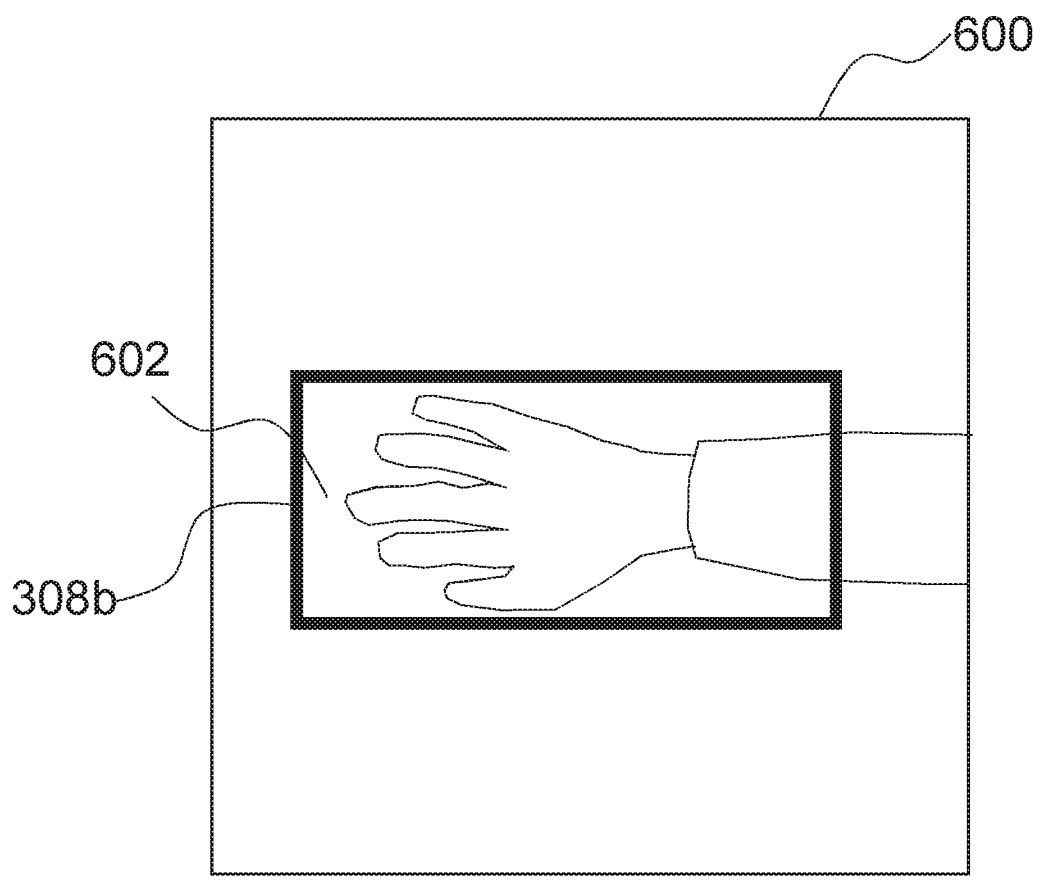
FIG. 6 a representation of an image, which may be a photograph or digital image, of an example object to be imaged by an imaging device according to one embodiment of the invention.

For example, FIG. 6 shows an example of an image 600 for which the controller 110 has determined that there is a background portion of the first image, between the foreground portion of the first image and the boundary 308, which exceeds a threshold amount in a region 602.

If, at block 410, the controller 110 determines that there is not a background portion of the first image, between the foreground portion of the first image and the boundary 308, which exceeds a threshold amount, then the controller proceeds directly to block 408.

If, however, the controller 110 determines that there is a background portion of the first image, between the foreground portion of the first image and the boundary 308, which exceeds a threshold amount, then the controller 110 proceeds to block 412.

At block 412, the controller 110 adjusts one or more edges of the boundary 308 to reduce an area of the first image encompassed by the boundary 308. For example, the controller 110 may move one or more of the three edges closest to a distal feature of the object 106 to be imaged towards the corresponding position of the predefined feature if an amount of background portion between the foreground portion and the respective edge of the boundary exceeds a threshold amount.

At block 414, the controller 110 again determines whether there is a background portion of the first image between the first part and the boundary 308 that exceeds a threshold amount.

If, at block 414, the controller 110 determines that there is a background portion of the first image, between the foreground portion of the first image and the boundary 308, that exceeds a threshold amount, then the controller 110 returns to block 412 and again adjusts one or more edges of the boundary 308 to reduce an area of the first image encompassed by the boundary 308 before proceeding again to block 414.

If, however, at block 414, the controller 110 determines that the amount of background portion of the first image, distal to an identified distal feature, between the first part and the boundary 308, is below the threshold amount, then the controller 110 proceeds to block 408 to end the refinement method 400. By performing steps 410 to 414 on the image 600 shown in FIG. 6, the controller 110 can reduce the region 602 of background between the foreground and the boundary 308 to adjust the boundary 308 as shown in FIG. 5. This ensures that while no part of the distal part of the object 106 is not imaged, the object 106 to be imaged is not unnecessarily exposed to excess radiation.

FIG. 6 shows an example of an image 600 for which the controller 110 has refined the boundary 308 using the method 400 described with reference to FIG. 4 to encompass all of the portions of the object 106 to be imaged that are of interest but to minimize a region 602 of background between the foreground and the boundary 308.

In some examples, where the object 106 is not connected to another object that is not to be imaged, the method 400 may be applied to all identified predetermined features of the object 106, rather than just a first (e.g. distal) part.

Furthermore, if the controller 110 identifies that a position of a predetermined feature relates to a proximal feature (such as a wrist of a human subject), the controller may, in relation to that predetermined feature, dispense with the method 400 described with reference to FIG. 4 in relation to the proximal feature. In doing so, the controller 110 may avoid unnecessarily expanding the boundary to encompass parts of the subject that are, for diagnostic purposes, not of interest, but by which the object 106 to be imaged (e.g. a hand of the subject) is connected to the rest of the subject's body.

In some examples, the controller 110 may adjust all edges of the boundary 308. In other examples, the controller 110 may adjust only portions of the boundary 308 for which a portion of the foreground meets the boundary 308.

The method 400 described above with reference to FIG. 4 comprises steps in which the controller 110 adjusts edges of the boundary to enlarge the area of the boundary and steps in which the controller 110 adjusts edges of the boundary to reduce the area of the boundary. However, in some examples, the controller 110 may only adjust edges of the boundary to enlarge the area of the boundary or only adjusts edges of the boundary to reduce the area of the boundary.

In some examples, as shown in FIGS. 3a to 3c and FIGS. 5 and 6, the boundary defines an area having four sides. The determination of the boundary may comprises determining a dimension of the area. For example, the controller 110 may determine lengths of one or more sides of the area and/or a dimension across the area, such as a length of a diagonal dimension of a rectangular area or dimensions of the major and minor axes of an elliptical area, for example.

While the invention has been illustrated and described in detail with the help of a preferred embodiment, the invention is not limited to the disclosed examples. Other variations can be deducted by those skilled in the art without leaving the scope of protection of the claimed invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of controlling one or more parameters of a medical imaging device including a radiation source unit, the method comprising:
   receiving image data representing a first image of an object to be imaged using the radiation source unit;
   detecting respective positions of respective features in the first image;
   determining a boundary of an imaging area of the object to be imaged, based upon the respective positions detected; and
   controlling one or more parameters of the radiation source unit based upon the boundary determined,
   wherein the detecting of the respective positions comprises:
      evaluating one or more portions of the first image with respect to a model of the respective features,
      assigning a probability value to each of the one or more portions of the first image based upon the one or more portions evaluated, and
      determining that one or more of the one or more portions of the first image corresponds with the respective feature based upon a corresponding probability value assigned.

2. The method of claim 1, further comprising:
   determining at least one of an object size and an object orientation of the object to be imaged, based upon the respective positions detected.

3. The method of claim 1, wherein the one or more parameters of the radiation source unit include at least one of
   a position of the radiation source unit, and
   one or more collimator settings of a collimator of the radiation source unit.

4. The method of claim 1, comprising:
   identifying a background portion of the first image and a foreground portion of the first image based upon data in the received image data representing one or more image channels; and
   determining the boundary based upon the identifying of the background portion of the first image and of the foreground portion of the first image.

5. The method of claim 2, comprising:
   determining object orientation based upon an angle of a line intersecting two or more of the respective positions detected; and
   orientating the boundary of the imaging area of the object to correspond with the object orientation determined.

6. The method of claim 2, wherein the one or more parameters of the radiation source unit include at least one of
   a position of the radiation source unit, and
   one or more collimator settings of a collimator of the radiation source unit.

7. The method of claim 5, wherein the one or more parameters of the radiation source unit include at least one of
   a position of the radiation source unit, and
   one or more collimator settings of a collimator of the radiation source unit.

8. The method of claim 5, comprising:
   identifying a background portion of the first image and a foreground portion of the first image based upon data in the received image data representing one or more image channels; and
   determining the boundary based upon the identifying of the background portion of the first image and of the foreground portion of the first image.

9. The method of claim 4, comprising:
   determining whether a first part of the foreground portion of the first image meets the boundary; and
   adjusting, in response to the determining indicating that the first part of the foreground portion of the first image meets the boundary, the boundary to encompass the first part of the foreground portion of the first image.

10. The method of claim 9, comprising:
    determining whether there is a background portion of the first image between the first part of the first image and the boundary; and
    adjusting, in response to the determining indicating that there is a background portion of the first image between the first part of the first image and the boundary, the boundary so as to relatively reduce a size of the background portion.

11. The method of claim 9, wherein the object to be imaged is a body part of a human or animal subject, the respective features include anatomical features of the subject, and the first part includes a distal end of the object to be imaged.

12. The method of claim 10, wherein the object to be imaged is a body part of a human or animal subject, the respective features include anatomical features of the subject, and the first part includes a distal end of the object to be imaged.

13. The method of claim 8, comprising:
determining whether a first part of the foreground portion of the first image meets the boundary; and
adjusting, in response to the determining indicating that the first part of the foreground portion of the first image meets the boundary, the boundary to encompass the first part of the foreground portion of the first image.

14. The method of claim 13, comprising:
determining whether there is a background portion of the first image between the first part of the first image and the boundary; and
adjusting, in response to the determining indicating that there is a background portion of the first image between the first part of the first image and the boundary, the boundary so as to relatively reduce a size of the background portion.

15. A medical imaging device, comprising:
a processor arranged to:
receive image data representing a first image of an object to be imaged using a radiation source unit of the medical imaging device;
determine a boundary of an imaging area of the object to be imaged, based upon respective positions of features in the first image, wherein to detect the respective positions of features in the first image, the processor being further arranged to
evaluate one or more portions of the first image with respect to a model of the respective features,
assign a probability value to each of the one or more portions of the first image based upon the one or more portions evaluated, and
determine that one or more of the one or more portions of the first image corresponds with the respective feature based upon a corresponding probability value assigned; and
control one or more parameters of the radiation source unit based upon the boundary determined.

16. The medical imaging device of claim 15, wherein the one or more parameters include at least one of a position and an orientation of the radiation source unit.

17. The medical imaging device of claim 15, wherein the radiation source unit includes a collimator to collimate a beam of radiation emitted from the radiation source unit, wherein the processor is further arranged to control one or more collimator settings based upon the boundary determined.

18. The medical imaging device of claim 15, further comprising a camera, arranged to generate the first image, the camera being separate from the radiation source unit.

19. The medical imaging device of claim 15, wherein the medical imaging device is an x-ray radiography device and wherein the radiation source unit comprises an X-ray source.

20. The medical imaging device of claim 15, wherein the processor is further arranged to:
detect respective positions of the respective features in the first image; and
determine the boundary of an imaging area of the object to be imaged, based upon the respective positions detected.

21. The medical imaging device of claim 16, wherein the radiation source unit includes a collimator to collimate a beam of radiation emitted from the radiation source unit, wherein the processor is further arranged to control one or more collimator settings based upon the boundary determined.

22. The medical imaging device of claim 16, further comprising a camera, arranged to generate the first image, the camera being separate from the radiation source unit.

23. The medical imaging device of claim 16, wherein the medical imaging device is an x-ray radiography device and wherein the radiation source unit comprises an X-ray source.

24. A non-transitory computer readable medium storing a computer program, loadable into a memory unit of a data processing system, including program code sections to enable the data processing system to execute a method when the computer program is executed in the data processing system, the method comprising:
receiving image data representing a first image of an object to be imaged using a radiation source unit;
detecting respective positions of respective features in the first image;
determining a boundary of an imaging area of the object to be imaged, based upon the respective positions detected; and
controlling one or more parameters of the radiation source unit based upon the boundary determined,
wherein the detecting of the respective positions comprises:
evaluating one or more portions of the first image with respect to a model of the respective features,
assigning a probability value to each of the one or more portions of the first image based upon the one or more portions evaluated, and
determining that one or more of the one or more portions of the first image corresponds with the respective feature based upon a corresponding Probability value assigned.

25. A method of controlling one or more parameters of a medical imaging device including a radiation source unit, the method comprising:
receiving image data representing a first image of an object to be imaged using the radiation source unit;
detecting respective positions of respective features in the first image;
determining a boundary of an imaging area of the object to be imaged, based upon the respective positions detected, the determining including
identifying a background portion of the first image and a foreground portion of the first image based upon data in the received image data representing one or more image channels, and
determining the boundary based upon the identifying of the background portion of the first image and of the foreground portion of the first image;
determining whether a first part of the foreground portion of the first image meets the boundary;
adjusting, in response to the determining indicating that the first part of the foreground portion of the first image meets the boundary, the boundary to encompass the first part of the foreground portion of the first image, to determine an adjusted boundary; and
controlling one or more parameters of the radiation source unit based upon the adjusted boundary.

26. A medical imaging device, comprising:
a processor arranged to:

receive image data representing a first image of an object to be imaged using a radiation source unit of the medical imaging device;

determine a boundary of an imaging area of the object to be imaged, based upon respective positions of features in the first image, wherein to determine the boundary, the processor is further arrange to identify a background portion of the first image and a foreground portion of the first image based upon data in the received image data representing one or more image channels, and determine the boundary based upon identification of the background portion of the first image and of the foreground portion of the first image;

determine whether a first part of the foreground portion of the first image meets the boundary;

adjust, in response to determining that the first part of the foreground portion of the first image meets the boundary, the boundary to encompass the first part of the foreground portion of the first image, to determine an adjusted boundary; and control one or more parameters of the radiation source unit based upon the adjusted boundary.

27. A non-transitory computer readable medium storing a computer program, loadable into a memory unit of a data processing system, including program code sections to enable the data processing system to execute a method when the computer program is executed in the data processing system, the method comprising:

receiving image data representing a first image of an object to be imaged using a radiation source unit;

detecting respective positions of respective features in the first image;

determining a boundary of an imaging area of the object to be imaged, based upon the respective positions detected, the determining including identifying a background portion of the first image and a foreground portion of the first image based upon data in the received image data representing one or more image channels, and determining the boundary based upon the identifying of the background portion of the first image and of the foreground portion of the first image;

determining whether a first part of the foreground portion of the first image meets the boundary;

adjusting, in response to the determining indicating that the first part of the foreground portion of the first image meets the boundary, the boundary to encompass the first part of the foreground portion of the first image, to determine an adjusted boundary; and controlling one or more parameters of the radiation source unit based upon the adjusted boundary.

* * * * *